(12) United States Patent
Dougal (10) Patent No.: US 9,108,044 B2
(45) Date of Patent: Aug. 18, 2015

(54) USE OF ELECTROMAGNETIC RADIATION IN THE TREATMENT OF SENSORY ORGANS

(75) Inventor: Gordon Rex Paterson Dougal, Durham (GB)

(73) Assignee: Virulite Distribution Limited, Durham (GB)

( * ) Notice: Subject to any disclaimer, the term of this patent is extended or adjusted under 35 U.S.C. 154(b) by 1364 days.

(21) Appl. No.: 11/917,288

(22) PCT Filed: Jun. 13, 2006

(86) PCT No.: PCT/GB2006/002153
§ 371 (c)(1),
(2), (4) Date: May 23, 2008

(87) PCT Pub. No.: WO2006/134339
PCT Pub. Date: Dec. 21, 2006

(65) Prior Publication Data
US 2008/0319516 A1 Dec. 25, 2008

(30) Foreign Application Priority Data

Jun. 14, 2005 (GB) .................................. 0512038.1

(51) Int. Cl.
*A61N 5/06* (2006.01)
*A61F 9/007* (2006.01)
(Continued)

(52) U.S. Cl.
CPC .............. *A61N 5/0603* (2013.01); *A61F 9/008* (2013.01); *A61F 9/0079* (2013.01); *A61M 21/00* (2013.01);
(Continued)

(58) Field of Classification Search
CPC .............. A61N 2005/0652; A61N 2005/0644;
A61N 2005/0645; A61N 2005/0648; A61N 2005/0659; A61N 2005/0629; A61N 2005/0642; A61N 2005/067; A61N 5/1017; A61B 5/6803; A61B 5/6821
USPC .................... 607/72–76, 88, 90, 91; 356/214; 351/205, 209, 246; 604/5.02; 128/898; 29/428
See application file for complete search history.

(56) References Cited

U.S. PATENT DOCUMENTS 3,473,868 A * 10/1969 Newman et al. ............... 351/210
3,533,683 A * 10/1970 Stark et al. ..................... 351/206
(Continued)

FOREIGN PATENT DOCUMENTS

DE 4 003 477 A1 8/1991
DE 4003477 A1 8/1991
(Continued)

OTHER PUBLICATIONS

Notification of Transmittal of the International Search Report and the Written Opinion of the International Searching Authority, or the Declaration corresponding to International Application No. PCT/GB2006/002153 mailed Nov. 10, 2006.
(Continued)

*Primary Examiner* — Cris L Rodriguez
*Assistant Examiner* — Matthew Saunders
(74) *Attorney, Agent, or Firm* — Myers Bigel Sibley & Sajovec, PA (57) ABSTRACT

A method of using and devices for delivering electromagnetic radiation of a selected wavelength for the treatment of conditions pertaining to cephalic sensory organs, in particular to treating conditions of the eye (ocular conditions) and conditions pertaining to the ear (otic conditions). The invention is in particular for the treatment of organelles associated with the acoustic and optic nerves and more particularly for the treatment of age related degeneration of such organelles. The invention also provides devices for treating ocular and otic conditions.

5 Claims, 2 Drawing Sheets

(51) Int. Cl.
*A61F 9/008* (2006.01)
*A61M 21/00* (2006.01)

(52) U.S. Cl.
CPC .............. *A61F 2009/00863* (2013.01); *A61M 2021/0027* (2013.01); *A61M 2021/0044* (2013.01); *A61M 2021/0055* (2013.01); *A61N 2005/0605* (2013.01); *A61N 2005/0647* (2013.01); *A61N 2005/0652* (2013.01); *A61N 2005/0659* (2013.01)

(56) References Cited

U.S. PATENT DOCUMENTS

| | | | |
|---|---|---|---|
| 4,641,349 A * | 2/1987 | Flom et al. | 382/117 |
| 4,858,609 A | 8/1989 | Cole | |
| 4,878,891 A | 11/1989 | Judy et al. | |
| 4,917,084 A | 4/1990 | Sinofsky | |
| 4,930,504 A | 6/1990 | Diamantopoulos et al. | |
| 4,931,053 A * | 6/1990 | L'Esperance et al. | 606/2 |
| 4,951,663 A | 8/1990 | L'Esperance, Jr. | |
| 5,066,291 A | 11/1991 | Stewart | |
| 5,259,380 A | 11/1993 | Mendes et al. | |
| 5,348,551 A | 9/1994 | Spears et al. | |
| 5,445,146 A * | 8/1995 | Bellinger | 607/89 |
| 5,464,436 A | 11/1995 | Smith | |
| 5,478,239 A * | 12/1995 | Fuerst et al. | 473/438 |
| 5,500,009 A | 3/1996 | Mendes et al. | |
| 5,507,716 A * | 4/1996 | LaBerge et al. | 600/27 |
| 5,527,350 A | 6/1996 | Grove et al. | |
| 5,630,811 A | 5/1997 | Miller | |
| 5,658,323 A | 8/1997 | Miller | |
| 5,707,403 A | 1/1998 | Grove et al. | |
| 5,743,901 A | 4/1998 | Grove et al. | |
| 5,784,145 A * | 7/1998 | Ghodse et al. | 351/205 |
| 5,805,267 A * | 9/1998 | Goldman | 351/203 |
| 5,818,048 A | 10/1998 | Sodickson et al. | |
| 5,849,035 A | 12/1998 | Pathak et al. | |
| 5,868,731 A | 2/1999 | Budnik et al. | |
| 5,913,883 A | 6/1999 | Alexander et al. | |
| 5,989,245 A | 11/1999 | Prescott | |
| 6,027,495 A | 2/2000 | Miller | |
| 6,063,108 A | 5/2000 | Salansky et al. | |
| 6,091,546 A * | 7/2000 | Spitzer | 359/618 |
| 6,113,237 A * | 9/2000 | Ober et al. | 351/210 |
| 6,149,272 A * | 11/2000 | Bergner et al. | 351/221 |
| 6,179,830 B1 | 1/2001 | Kokubu | |
| 6,193,373 B1 * | 2/2001 | Apple et al. | 351/221 |
| 6,299,308 B1 * | 10/2001 | Voronka et al. | 351/210 |
| 6,334,683 B2 * | 1/2002 | Apple et al. | 351/221 |
| 6,358,272 B1 * | 3/2002 | Wilden | 607/89 |
| 6,471,716 B1 | 10/2002 | Pecukonis | |
| 6,663,659 B2 | 12/2003 | McDaniel | |
| 6,887,260 B1 | 5/2005 | McDaniel | |
| 6,986,765 B2 * | 1/2006 | Sumiya et al. | 606/10 |
| 7,060,061 B2 | 6/2006 | Altshuler et al. | |
| 7,730,893 B2 | 6/2010 | Dougal | |
| 2001/0028309 A1 * | 10/2001 | Torch | 340/575 |
| 2003/0058492 A1 * | 3/2003 | Wakiyama | 359/20 |
| 2004/0093043 A1 | 5/2004 | Edel et al. | |
| 2004/0122491 A1 * | 6/2004 | Strong | 607/88 |
| 2004/0225340 A1 * | 11/2004 | Evans | 607/88 |
| 2005/0024853 A1 | 2/2005 | Thomas-Benedict | |
| 2005/0187579 A1 | 8/2005 | Danek et al. | |
| 2005/0234383 A1 | 10/2005 | Dougal | |
| 2006/0271131 A1 | 11/2006 | Passy et al. | |
| 2007/0129778 A1 | 6/2007 | Dougal | |

FOREIGN PATENT DOCUMENTS

| | | |
|---|---|---|
| DE | 29 820 468 U1 | 4/2000 |
| DE | 29820468 U1 | 4/2000 |
| DE | 10 049 068 A1 | 9/2001 |
| DE | 10049068 A1 | 9/2001 |
| DE | 10201904 A1 | 7/2003 |
| DE | 10 237 620 A1 | 3/2004 |
| DE | 10237620 A1 | 3/2004 |
| EP | 0 533 585 A1 | 3/1993 |
| EP | 0 695 559 A2 | 2/1996 |
| EP | 01021223 * | 10/2004 |
| GB | 2360461 A | 9/2001 |
| GB | 2 415 387 A | 12/2005 |
| KR | 20-0297648 | 12/2002 |
| WO | WO 97/47993 A1 | 12/1997 |
| WO | WO 98/23329 A1 | 6/1998 |
| WO | WO 99/19024 A | 4/1999 |
| WO | WO 99/19024 A1 | 4/1999 |
| WO | WO 01/30292 A2 | 5/2001 |
| WO | WO 04/000150 A1 | 12/2003 |
| WO | WO 2006/028465 A1 | 3/2006 |
| WO | WO 2006/030403 | 3/2006 |
| WO | WO 2006/108093 A2 | 10/2006 |
| WO | WO 2009/038720 A2 | 3/2009 |

OTHER PUBLICATIONS

Abergel et al. "Laser Treatment of Keloids: A Clinical Trial and an In Vitro Study with Nd:YAG Laser" *Lasers in Surgery and Medicine* 4:291-295 (1984).

Abergel et al. "Nonthermal Effects on Nd:YAG Laser on Biological Functions of Human Skin Fibroblasts in Culture" *Lasers in Surgery and Medicine* 3:279-284 (1984).

Agaiby et al. "Laser modulation of angiogenic factor production by T-lymphocytes" *Lasers in Surgery and Medicine* 26:357-363 (2000).

Almeida-Lopes et al. "Comparison of the Low Level Laser Therapy Effects on Cultured Human Gingival Fibroblasts Proliferation Using Different Irradiance and Same Fluence" *Lasers in Surgery and Medicine* 29:179-184 (2001).

Castro et al. "Effects of the Nd:YAG Laser on DNA Synthesis and Collagen Production in Human Skin Fibroblast Cultures" *Annals of Plastic Surgery* 11(3):214-222 (1983).

Combined Search and Examination Report for United Kingdom Application No. GB0912206.0 mailed on Nov. 10, 2009.

Davis, Christopher C., *Laser & Electro-Optics*, Cambridge University Press, p. 289 (1996).

Dougal et al. "A pilot study of treatment of herpes labialis with 1072 nm narrow waveband light" *Clinical and Experimental Dermatology* 25:149-154 (Mar. 1, 2001).

International Preliminary Report on Patentability and Written Opinion dated Jan. 27, 2011 for PCT/GB2009/050848.

International Preliminary Report on Patentability and Written Opinion of the International Searching Authority for International Application No. PCT/EP2010/054762; Date of Mailing: Oct. 27, 2011; 16 pages.

International Search Report and Written Opinion of the International Searching Authority for International Application No. PCT/EP2010/054762; Date of Mailing: Jun. 28, 2010; 16 pages.

International Search Report Corresponding to International Application No. PCT/GB2005/002433; Date of Mailing: Aug. 18, 2005; 4 pages.

Kreisler et al. "Low Level 809-nm Diode Laser Induced In Vitro Stimulation of the Proliferation of Human Gingival Fibroblasts" *Lasers in Surgery and Medicine* 30:365-369 (2002).

Loevschall et al. "Effect of Low Level Diode Laser Irradiation of Human Oral Mucosa Fibroblasts in Vitro" *Lasers in Surgery and Medicine* 14:347-354 (1994).

Mohanty et al. Comet Assay Measurements of DNA Damage in Cells by Laser Microibeams and Trapping Beams with Wavelengths Spanning a Range of 308 NM to 1064 NM *Radiation Research* 157(4):378-385 (2002).

Mokhtar et al. "Double-Blind, Placebo-Controlled Investigation of the Effect of Combined Phototherapy/Low Intensity Laser Therapy Upon Experimental Ischaemic Pain in Humans" *Lasers in Surgery and Medicine* 17:74-81 (1995).

Pereira et al. "Effect of Low-Power Laser Irradiation on Cell Growth and Procollagen Synthesis of Cultured Fibroblasts" *Lasers in Surgery and Medicine* 31:263-267 (2002).

(56) References Cited

OTHER PUBLICATIONS

Sakihama, Hideki "Effect of a Helium-Neon Laser on Cutaneous Inflammation" T*he Kurame Medical Journal* 42:299-305 (1995).
Spicer et al.; Lasers in Dermatology, Journal of the American Academy of Dermatology, Jan. 1996.
Steller et al.; Lasers in Surgery, Laser Applications in Medicine and Biology, vol. 2., 1974 pp. 246-249.
Vecchio et al. "A Double-Blind Study of the Effectiveness of Low Level Laser Treatment of Rotator Cuff Tendinitis" *British Journal of Rheumatology* 32:740-742 (1993).

* cited by examiner

USE OF ELECTROMAGNETIC RADIATION IN THE TREATMENT OF SENSORY ORGANS

RELATED APPLICATIONS

The present application is a 35 U.S.C. §371 national phase application of PCT International Application No. PCT/GB2006/002153, having an international filing date of Jun. 13, 2006 and claiming priority to Great Britain Patent Application No. 0512038.1, filed Jun. 14, 2005, the disclosures of which are incorporated herein by reference in their entireties. The above PCT International Application was published in the English language and has International Publication No. WO 2006/134339.

FIELD OF THE INVENTION

The present invention relates to the use of electromagnetic radiation of a selected wavelength for the treatment of conditions pertaining to cephalic sensory organs, in particular to treating conditions of the eye (ocular conditions) and conditions pertaining to the ear (otic conditions). The invention is in particular for the treatment of organelles associated with the acoustic and optic nerves and more particularly for the treatment of age related degeneration of such organelles. The invention also provides devices for treating ocular and otic conditions.

BACKGROUND TO THE INVENTION

Macular degeneration is a medical condition where the light sensing cells in the macula malfunction and over time cease to work it is the leading cause of central vision loss (blindness) for those over the age of fifty. There are two basic types of the disease: Standard Macular Degeneration (MD) and Age Related Macular Degeneration (ARMD), with ARMD being the most common form of the condition. Macular degeneration that is not age related is most commonly caused by an inherited condition. These forms are sometimes called Juvenile macular degeneration (JMD). In macular degeneration the final form results in missing or blurred vision in the central, reading part of vision. The outer, peripheral part of the vision remains intact. The treatment for such conditions is by drug therapy such as pegaptanib (Macugen™), ranibizumab (Lucentis™), anecortave (Retaane™), bevacizumab (Avastin™), squalamine (Evizon™) and statins, a family of drugs used for reducing cholesterol levels.

Age-related hearing loss (presbycusis) involves a progressive loss of hearing, beginning with high-frequency sounds such as speech. It is unknown whether a specific cause such as noise trauma leads to presbycusis, but there appears to be a genetic predisposition. Age-related hearing loss tends to occur in families. The disorder occurs in about 25% of people aged 65 to 75 and in 70% to 80% of those over age 75. There is no known cure for age-related hearing loss. Treatment is focused on functional improvement such as hearing aids, which provide amplification. Developing skills such as lip reading and using visual cues may aid communication, but these may be difficult skills for older people to learn.

It is known from the prior art that electromagnetic radiation centred around a wavelength of 1072 nm is an effective treatment for cold sores and improves the immune response to many infections (WO 9919024). It is also known from the prior art that 1072 nm light is also effective at reducing wrinkles and improving the elasticity of skin.

In the present invention we have found that electromagnetic radiation of a selected wavelength is also effective at treating ocular and otic conditions and provides an alternative therapy for such conditions.

BRIEF SUMMARY OF THE DISCLOSURE

According to a first aspect of the invention there is provided a method of treating ocular and/or otic conditions and/or organelles associated with the optic and acoustic nerves and associated organelles, the method comprising exposing the affected organ or organelle to divergent electromagnetic radiation of wavelength between 900 nm and 1300 nm.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Reference herein to "organelles associated with the optic and acoustic nerves and associated organelles" includes the pigment layer, photoreceptors and ganglion cells of the retina, in addition, includes the external auditory meatus, tympanic membrane, middle ear, semi-circular canals, cochlea and VIIth cranial nerve.

Preferably, the method of treatment of the present invention is for the treatment of any one or more of the following conditions selected from the group comprising ARMD, poor visual acuity, optic nerve disorders, posterior uveitis, presbycusis, tinnitus, vertigo, conditions affecting the physiological characteristics of the organ of corti in the cochlea, ear and acoustic nerves and associated organelles.

The use of divergent electromagnetic radiation of wavelength between 900 nm and 1300 nm is as a therapy for the treatment of organelles associated with the optic and acoustic nerves. We have found using the method of the present invention that hearing was significantly improved. We have also found that the method of the present invention improves cell viability.

According to a second aspect of the invention there is provided use of divergent electromagnetic radiation of wavelength between 900 nm and 1300 nm for the treatment of otic and/or ocular conditions and organelles associated with the optic and acoustic nerves.

In the present invention we have been able to establish that low intensity electromagnetic radiation of small bandwidth (around 10 nm to 120 nm) is effective in treating conditions such as ARMD, posterior uveitis, presbycusis and tinnitus.

Preferably, the divergent light is between 10 to 50°. By divergent it meant that the electromagnetic radiation emitted from the electromagnetic source has a divergent half angle of at least 5°.

Preferably divergence of the electromagnetic radiation is in the range 15 to 25° half angled divergent.

The present invention is concerned with a method of treating the optic and acoustic nerve and associated organelles with divergent electromagnetic radiation having a wavelength in the range from visible to infra red.

Preferably, the wavelength is centred around 940 nm, 950 nm, 1040 nm, 1060 nm, 1072 nm and 1267 nm or more preferably is a combined wavelength of 1072 nm and 1267 nm with the optical intensity of the wavelengths in the same ratio as the peaks in the transmission spectrum of the water molecule.

The water molecule that has a range of electromagnetic radiation wavelengths passed through it will produce several transmission peaks. These transmission peaks are a associated with the preferred therapeutic electromagnetic radiation wavelength range of the invention and thus implies a role for the water molecule in the general mechanism of action.

Our studies have shown that wavelengths centred around those wavelengths specified above and especially around 940 nm, 950 nm, 1040 nm, 1060 nm, 1072 nm or 1267 nm are particularly effective in improving visual acuity in patients with ARMD and improve hearing in patients with presbycusis. In particular our evidence suggests that wavelengths of 1072 nm and 1267 nm are particularly effective and it is of note that these two wavelengths correspond to the peak emission wavelengths of a water molecule's light transmission profile and thus we believe that the mechanism of action is related to water and possibly cell membranes and the peak spectral emission of singlet oxygen.

Preferably, the electromagnetic radiation is continuous or pulsed.

Preferably, when the electromagnetic radiation is continuous the intensity is at least 500 $\mu$Watts/cm$^2$ and up to 500 mWatts/cm$^2$.

Preferably, when the combined electromagnetic radiation is pulsed the intensity is at least 500 $\mu$Watts/cm$^2$ peak power and the average power is up to 500 mWatts/cm$^2$. The average power is the peak power multiplied by the proportion of the total time that the radiation is applied. For instance if the peak power is 500 $\mu$Watts/cm$^2$ and is pulsed for 10 $\mu$seconds at a frequency of 600 Hz then the average power is 30 $\mu$Watts/cm$^2$.

Due to the proximity of the light sources to delicate neural/nerve tissue thermal heating of the target tissue should be avoided. Preferably when the electromagnetic radiation is pulsed the average power of the intensity is in the region of 50-100 $\mu$g Watts/cm$^2$. We have found that the power may suitably range from 500 pWatts/cm$^2$ peak to 500 mWatts/cm$^2$ continuous or peak power when applied to the eye/ear. Typically 20 mWatts/cm$^2$ are used on skin but this value is dependent on how fat or muscular the subject is.

Preferably when the electromagnetic radiation is pulsed it is applied for periods of at least 10-15 $\mu$seconds and more preferably is applied at a frequency/repetition rate in the range 100-1000 Hz more preferably still the frequency/repetition rate is at, or about, 600 Hz. Our studies have shown that the electromagnetic radiation can be either coherent or non-coherent the clinical outcomes are not affected by this parameter.

Preferably the electromagnetic radiation is applied to the affected area for at least 30 seconds and up to a few minutes. A typical exposure time is in the region of 3 minutes however this time is increased according to the individual's requirements and exposure could be up to 10 minutes.

It should be appreciated that the power source emitting the electromagnetic radiation will have to produce more than the required intensity for the clinical effect since we have shown that approximately 95% of the applied therapeutic amount of light is lost during treatment. Thus the intensity of applied radiation is typically corrected for when carrying out a treatment.

From the foregoing it is understood that the electromagnetic radiation may be directed to the target site either continuously or in a switched (pulsed) manner. The main benefit of switching enables power conservation and facilities much higher peak power output, thereby improving therapeutic response.

Preferably, the electromagnetic radiation therapy source includes means for reducing the amount of ambient radiation, which impinges on the treatment site.

Preferably, the electromagnetic radiation source comprises light emitting diodes or laser diodes. The radiation from such devices can be electrically operated or the radiation can be delivered to an applicator via a fibre-optic delivery system.

Preferably, the radiation source emitter includes PN junctions arranged to emit radiation with a wavelength centring at or about the previously mentioned specified wavelengths in the defined ratio of light output. A single light diode assembly may include a plurality of orientated junctions. Infrared emitting diodes may be arranged not only to emit radiation at a specific frequency but also to emit a high intensity divergent beam. The divergent light may also be derived from light emitting polymers.

The electromagnetic radiation is applied at a low intensity such that no thermal damage or heating is caused to the tissue, nerve or organ around the treatment area. In this way, the method of the present invention differs from the prior art use of electromagnetic radiation as the effects are non-thermal and avoid thermolysis. In addition the present invention is counter-intuitive to bio-stimulation since the concept of enhanced replication and synthesis is positively avoided.

According to a third aspect of the invention there is provided a portable light emitting device for the treatment of the ear, acoustic nerve and associated organelles, the device comprising:

(i) a moulded portion for insertion into an ear canal, the moulded portion having an opening at one end, which when inserted into the ear canal is adjacent an external aspect of the tympanic membrane and through which electromagnetic radiation can pass and a receiving portion positioned in the same anatomical plane as a pinna for receiving power from a power source, (ii) at least one light emitting means that produces divergent electromagnetic radiation of wavelength from 900 nm to 1300 nm, and (iii) a power means for providing power to the power source.

Preferably, the device further includes any one or more of the following features:

(i) an optical monitoring sensor for ensuring the light output is correct;

(ii) a thermal sensor for ensuring the temperature of the device does not exceed safe limits;

(iii) a frequency modulator for changing the frequency of a pulsed exposure or for switching to continuous exposure;

(iv) a timing means for ensuring that the period of treatment is regulated;

(v) a safety cut-out means optionally in the form of an alarm or cut-off switch which is operable when operational limits are exceeded or when the therapy period has expired.

Preferably, the power source to the light emitting means is electrical or is a fibre-optic.

Preferably, the power means is a battery or is mains electricity.

Preferably, the light emitting means is a LED or more preferably a plurality of LEDs. It will be appreciated that the light emitting means of the present invention may also be a laser light source.

Preferably, the light emitting means are positioned approximately centrally at the end of the moulded portion. An approximate central position ensures accurate irradiation of the middle and inner ear when in use. The light emitting means may be embedded in the moulded portion or may be housed with and allowed to protrude. The light emitting means are suitably sized so they may be accommodated into a mould similar to that made for hearing aides.

Preferably, the electromagnetic radiation impacts directly onto the tympanic membrane.

Preferably, in the instance of a plurality of light emitting means they are focused centrally. For example, a series of a 3 by 3 row of LEDS or fibre optics are arrange so that the central LED or fibre optic emits directly in a straight line towards the eardrum whereas the surrounding eight LEDs or fibre optics are focused towards the central one.

Preferably, the device may also comprise at least one or more PN junctions arranged to emit radiation with a wavelength centring at 1072 nm or 1267 nm and may be a laser device.

Preferably, the moulded portion is partially constructed of a resiliently deformable material or is coated or covered in such a material to ensure both a close fit within the ear canal and comfort to a user. A suitable material is rubber or foam. It will be appreciated that the moulded portion is transparent and is of a suitable size and shape to not only accommodate component parts but to fit within an ear canal.

Preferably, the device further includes a securing means for securing the device to a user's ear. The securing means may take the form of a loop or U shaped portion which can be attached to the pinna.

Preferably the device further includes any one or more of the features hereinbefore described with reference to the first and second aspects of the invention.

According to a fourth aspect of the invention there is provided a portable light emitting device for the treatment of the eye, optic nerve and associated organelles, the device comprising:
i) a housing comprising a cut-out portion or notch for accommodating a nasal bridge when in position on a user, the housing also comprises a first projecting portion for contacting a user's inferior orbital ridge and second projecting portion for contacting a user's superior orbital ridge when in position on a user,
ii) at least one visible light emitting means positioned approximately centrally within the housing so that when light is emitted to a user's eye the visible is in the same axis as the user's pupil;
iii) at least two light emitting means that produces divergent electromagnetic radiation of wavelength from 900 nm to 1300 nm, and being positioned within the housing either side of the central visible light emitting means, the at least two light emitting means that produce electromagnetic radiation being angled with respect to a user's eye so that they are not in the same axis as the pupil; and
iv) a power means for providing power to the power source.

It will be appreciated that the device for treating the eye when in position and in use effectively surrounds the eye and nests within the eye socket so that all light can be directed efficiently to the sclera and eye ball surface.

Preferably, the second projecting portion which rests or is in contact with a user's superior orbital ridge is resilient, that is to say it may be spring loaded so as to facilitate lifting or stretching of loose skin on the upper thus exposing a greater area of sclera to the divergent invisible infrared light. By supporting the loose skin above the eye the surface area of the sclera is increased through which the therapeutic infrared light can penetrate to globe.

Preferably, the visible light emitting means is positioned so that in use the visible light irradiates the cornea, causing the pupil to constrict and hence improve the safety of irradiating the eye with invisible infrared electromagnetic radiation.

Preferably, the electromagnetic radiation light emitting means are orientated within the housing so that they are defocused and are not in the optic axis of the pupil, this is a safety feature preventing possible optical damage to the macula.

Preferably, the device comprises a plurality of electromagnetic radiation light emitting means in cluster form each side of the central visible light emitting means.

Preferably, in use the visible light is pulsed out of phase to the infrared light so as not affect the clinical efficacy of the infrared light.

Preferably, the device further includes any one or more features hereinbefore described with reference to the first, second or third aspects of the invention.

DETAILED DESCRIPTION

Figure 1:
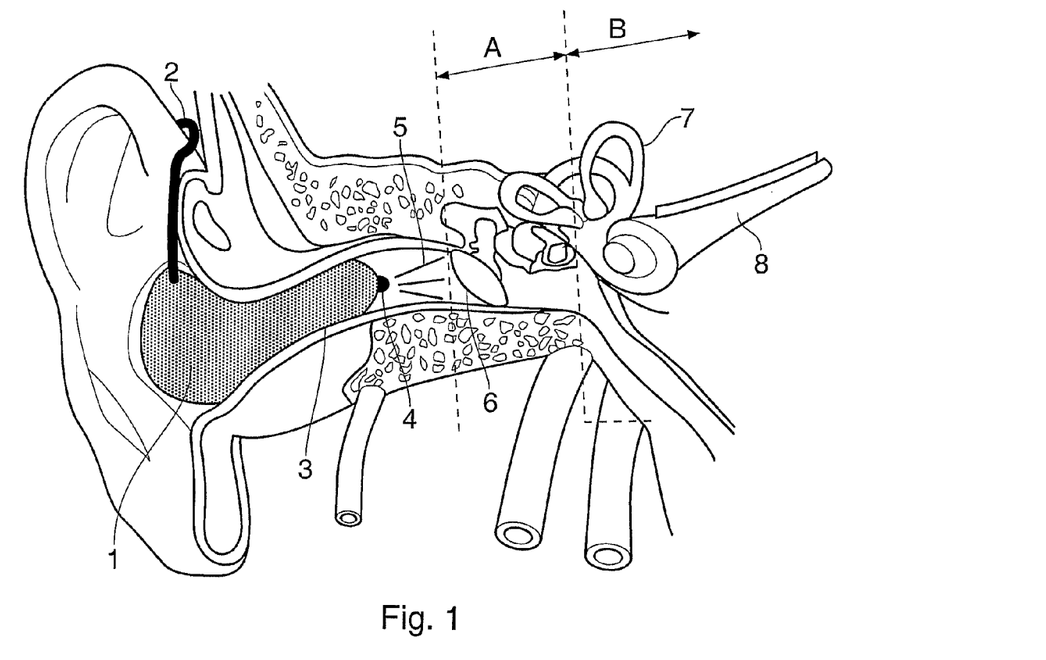
FIG. 1 shows a through section of a device of the present invention when inserted into a human ear.

Referring to FIG. 1 in one embodiment of the invention the device (1) is for insertion into an ear canal (3). The device is a portable electromagnetic radiation emitting device which can be either battery or mains operated. An electrical or fibre optic power source (2) provides power to the end (4) which comprises a plurality of light emitting means in the form of LEDs or laser lights which irradiate outwards (5) and towards the ear drum or tympanic membrane (6) to the middle (A) and inner (B) ear. The electromagnetic radiation passes towards the semicircular canals (7) or balance centre and also to the acoustic nerve (8). The light emitting means (4) of the device are small enough to be moulded into a mould similar to that made for hearing aides. When in use the electromagnetic radiation is this irradiated on primarily the tympanic membrane but also can pass to other organelles in the middle and inner ear. The device (4) within the moulded body also includes optical monitoring sensors ensuring the light output is correct together with thermal sensors ensuring the temperature of the device does not exceed safe limits.

Figure 2:
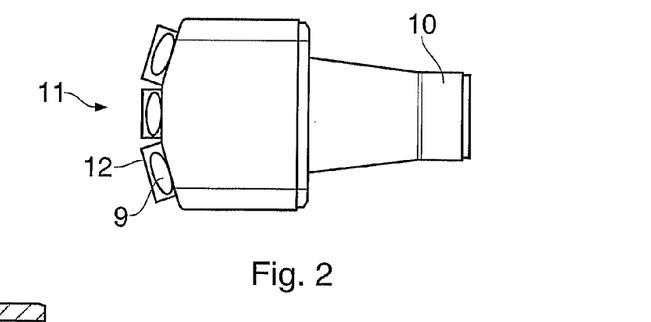
FIG. 2 shows a side view of the device of FIG. 1.
Figure 3:
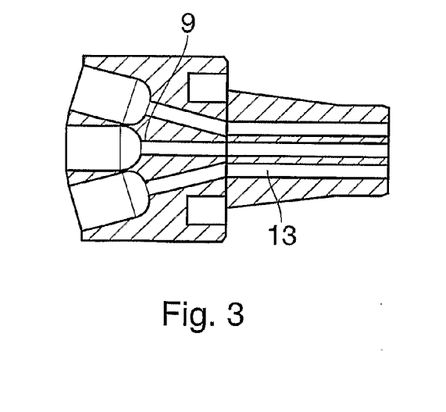
FIG. 3 shows a cut through section of the device of FIG. 2.

With regard to FIG. 2 there is shown the device (1) stripped of its coating or surface layer, end (10) is the portion adjacent an external aspect of the tympanic membrane and is the portion, in use, resting in the external auditory canal. The end (11) is the portion in the same anatomical plane as the pinna and comprises a number of light emitting devices (9) each provided with individual transparent safety caps (12). In section (FIG. 3) electrical conducting wires or fibre optics (13) feed power from the light emitting devices (9) to irradiate the tympanic membrane and hence other organelles of the ear.

Figure 4:
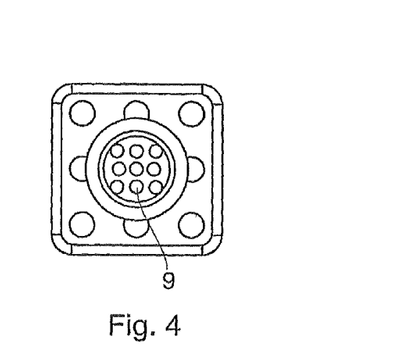
FIG. 4 shows a front end view of the device of FIG. 1.
Figure 5:
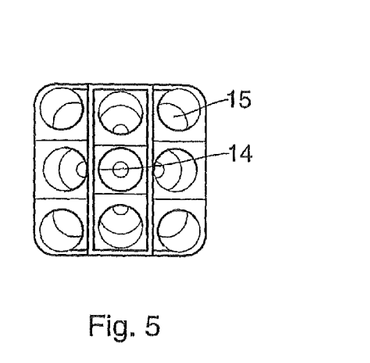
FIG. 5 shows an exploded diagram of the central portion of FIG. 4.

A front end on view of end 4 (FIG. 4) shows an arrangement of LEDs or laser lights (9) that are arranged so that the central LED or fibre optic light (14) is centrally focussed whereas surrounding LEDs or fibre optics are angled so that their emissions are directed centrally towards (14) so as to concentrate the emission.

Figure 6:
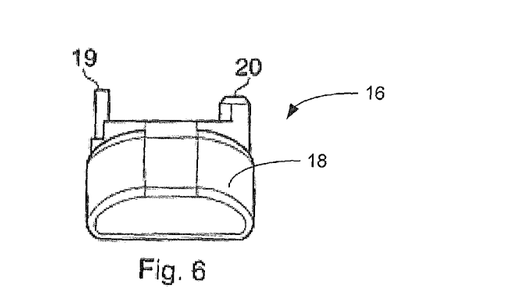
FIG. 6 shows a front view of a device of the present invention to treat the eyes.
Figure 7:
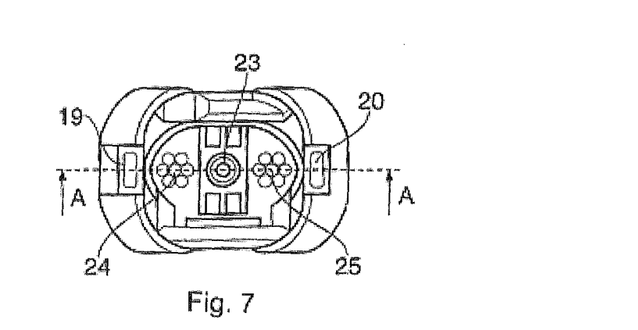
FIG. 7 shows an internal view of FIG. 6.

The device (16) of the invention for treating the eye is shown in FIGS. 6-7. Housing (18) is provided with a notch suitable shaped for accommodating a user's nasal bridge. The device also includes a first projection portion (20) which in use rests on the inferior orbital ridge, and a second projection portion (19) which in use rests on a the superior orbital ridge. The part that rests on the superior orbital ridge (19) is spring loaded which facilitates the loose skin of the upper lid being lifted thus exposing a greater area of sclera to the divergent invisible infrared light. Forming part of the housing are portions which house the off-centre electromagnetic radiation light emitting means. FIG. 6 shows a front view of the device. A centrally positioned visible light emitting means (23) emits visible light in to a user's pupil, it being in the same axis as the pupil. Positioned either side in portions (20 and 21) are a plurality of infrared LEDs (24) and (25) which being off-set direct the infrared light towards the sclera. The device is so arranged in order to causing the pupil to constrict (by direct visible light irradiation) and hence improve the safety of irradiating the eye whilst defocusing the invisible infrared electromagnetic radiation to prevent possible optical damage to the macula and other organelles.

When the device is viewed in direction A-A (FIG. 9), the series of LEDs (25 and 26) can be seen to be positioned either side of the visible light emitting means and off-set for the reasons above.

When the device is viewed in direction A-A (FIG. 7), the series of LEDs (25 and 26) can be seen to be positioned either side of the visible light emitting means and off-set for the reasons above.

EXAMPLE 1

We have evaluated the effect of 1072 nm light applied to the tympanic membrane and its effect on in improving hearing. Light sources were 1070 nm LED, directed into a large core fibre optic, which was encapsulated in an external auditory canal mould. The fibres were arranged so that they directed the 1072 nm light at the tympanic membrane and thence to the inner ear.

12 volunteers were selected with bilateral, largely symmetrical hearing loss. Audiometry was carried out twice to ensure accuracy of the results. Any patient with a result greater than 10 dB difference between the Audiometry was excluded.

The volunteers were then randomised to either receive an active light source in either the right or left ears and a placebo light source in the other ear.

The volunteers were then required to insert the applicator into their ears twice a day for a treatment period of 6 minutes. After 2 months the Audiogram was repeated.

Table 1 below shows the average improvement in hearing in db ("−" sign indicates a deterioration)

|  | Frequency | | | | | | |
| --- | --- | --- | --- | --- | --- | --- | --- |
|  | 500 Hz | 1 Khz | 2 Khz | 3 Khz | 4 Khz | 6 Khz | 8 Khz |
| Control ear (dB) | 0 | 2 | 3 | 1 | 0 | 4 | −6 |
| Active Ear (dB) | 5 | 12 | 9 | 13 | 5 | 6 | 0 |

It was noticed that the average improvement in hearing decreased with increasing frequency and this is thought to be related to the anatomy of the cochlea—less penetration of the light at the narrow high frequency end.

These results show that 1072 nm light is an effective method of reversing age related hearing loss when applied directly to the tympanic membrane.

EXAMPLE 2

We have evaluated of 1072 nm light applied to the retina to improve age related macula degeneration. A method was derived, using the device of the present invention, of constricting the pupil with visible light whilst shining the 1072 nm light through the sclera onto the retina thus removing any risk of optical eye injury.

Light sources were 1070 nm LED, directed obliquely to the optical axis of the eye. The visible light was switched "on" only when the pulsed 1072 nm light was "off", thus the two wavelengths of light would not interfere with each other. The repetition rate was high enough for the eye to perceive the lights as "on" continually.

12 volunteers were selected with bilateral, largely symmetrical age related macula degeneration. Visual acuity was carried out twice. The volunteers were then randomised to either receive an active light source in either the right or left eye and a placebo light source in the other eye.

The volunteers were then required to apply the applicator into their eyes twice a day for a treatment period of 6 minutes. After 2 months the Visual acuity was repeated.

Table 2 below shows the results on average improvement in vision, we have concluded that 1072 nm light is an effective method of reversing age related macula degeneration.

|  | Snellen chart |
| --- | --- |
| Control eye | 0 |
| Active eye | 1.2 lines |

The invention claimed is:

1. A portable battery operated light emitting device for the treatment of the eye, optic nerve and associated organelles, the device comprising:
(i) a housing comprising a cut-out portion or notch for accommodating a nasal bridge when in position on a user, the housing also comprises a first projecting portion for contacting a user's inferior orbital ridge and second projecting portion for contacting a user's superior orbital ridge when in position on a user;
(ii) at least one visible light emitting source positioned approximately centrally within the housing so that when pulsed light is emitted directly to a user's eye, a visible portion of emitted light from the at least one visible light emitting source is in the same axis as the user's pupil, to cause the pupil to contract, the visible light being emitted only when pulsed divergent light is not emitted; and (iii) at least two light emitting source that produce pulsed divergent electromagnetic radiation of wavelengths centered at 1072 nm, and being positioned within the housing on either side of the central visible light emitting source so as to direct the electromagnetic radiation centered at 1072 nm to the sclera oblique to the pupillary optical axis and deliver it to the retina, the at least two light emitting sources that produce electromagnetic radiation being angled with respect to a user's eye so that they are not in the same axis as the pupil such that the at least one visible light emitting source causes the user's pupil to constrict out of phase with the divergent electromagnetic radiation of wavelengths centered at 1072 nm to the user's pupil by the at least two light emitting sources so that electromagnetic radiation of wavelengths centered at 1072 nm are only emitted when the visible light is not emitted.

2. The device according to claim 1 wherein the second projecting portion which rests or is in contact with a user's superior orbital ridge is resilient or is spring loaded.

3. The device according to claim 1 wherein the at least two light emitting sources are orientated within the housing so that they are defocused and are not in the optic axis of the pupil.

4. The device according to claim 1 wherein the at least two light emitting sources comprises a plurality of electromagnetic radiation light emitting sources in cluster form positioned on each side of the central visible light emitting means.

5. The device according to claim 1, further comprising a frequency modulator for phasing the at least one visible light emitting source and the at least two light emitting sources that produce pulsed divergent electromagnetic radiation of wavelengths centered at 1072 am so that the visible light from the at least one visible light emitting source is pulsed out of phase with the infrared light from the at least two light emitting sources that produce pulsed divergent electromagnetic radiation of wavelengths centered at 1072 nm so that a user's eye receives only either visible light or electromagnetic radiation centered at 1072 nm at any one point in time.

* * * * *

UNITED STATES PATENT AND TRADEMARK OFFICE
CERTIFICATE OF CORRECTION

PATENT NO.        : 9,108,044 B2                                           Page 1 of 1
APPLICATION NO.   : 11/917288
DATED             : August 18, 2015
INVENTOR(S)       : Dougal It is certified that error appears in the above-identified patent and that said Letters Patent is hereby corrected as shown below:

In the Specification:
Column 2, Lines 35-36: Please correct "and VII-Ith cranial nerve"
　　　　　　　　　　　to read -- and VIIIth cranial nerve --.

Column 7, Lines 36-39: Please delete paragraph as it is a duplicate of the paragraph
　　　　　　　　　　　immediately following.

In the Claims:
Column 9, Claim 1, (iii), Line 4: Please correct "two light emitting source"
　　　　　　　　　　　to read -- two light emitting sources --.

Column 10, Claim 5, Line 14: Please correct "at 1072 am" to read -- at 1072 nm --.

Signed and Sealed this
Twenty-sixth Day of April, 2016

Michelle K. Lee
*Director of the United States Patent and Trademark Office*